United States Patent [19]
Bryant et al.

[11] 4,277,627
[45] Jul. 7, 1981

[54] HYDROFORMYLATION PROCESS

[75] Inventors: David R. Bryant, South Charleston; Ernst Billig, Charleston, both of W. Va.

[73] Assignee: Union Carbide Corporation, New York, N.Y.

[21] Appl. No.: 151,293

[22] Filed: May 19, 1980

Related U.S. Application Data

[63] Continuation of Ser. No. 762,336, Jan. 25, 1977.

[51] Int. Cl.³ ............................................. C07C 45/50
[52] U.S. Cl. .................................. 568/454; 252/431 P
[58] Field of Search ...................... 568/454; 252/431 P

[56] References Cited
U.S. PATENT DOCUMENTS

| | | | |
|---|---|---|---|
| 3,527,809 | 9/1970 | Pruett et al. | 568/454 |
| 3,644,446 | 2/1972 | Booth et al. | 568/454 |

Primary Examiner—Werren B. Lone
Attorney, Agent, or Firm—Reynold J. Finnegan

[57] ABSTRACT

A process for the hydroformylation of alpha-olefins employing a rhodium catalyst complexed with carbon monoxide and a triarylphosphine wherein the intrinsic deactivation of the rhodium catalyst which occurs under hydroformylation conditions is inhibited or substantially prevented by determining and correlating the reaction conditions of temperature, carbon monoxide partial pressure and the free triarylphosphine: catalytically-active rhodium metal mole ratio. These conditions can be determined from a mathematical relationship between the combination of these variables and the stability of the rhodium complex catalyst.

17 Claims, 5 Drawing Figures

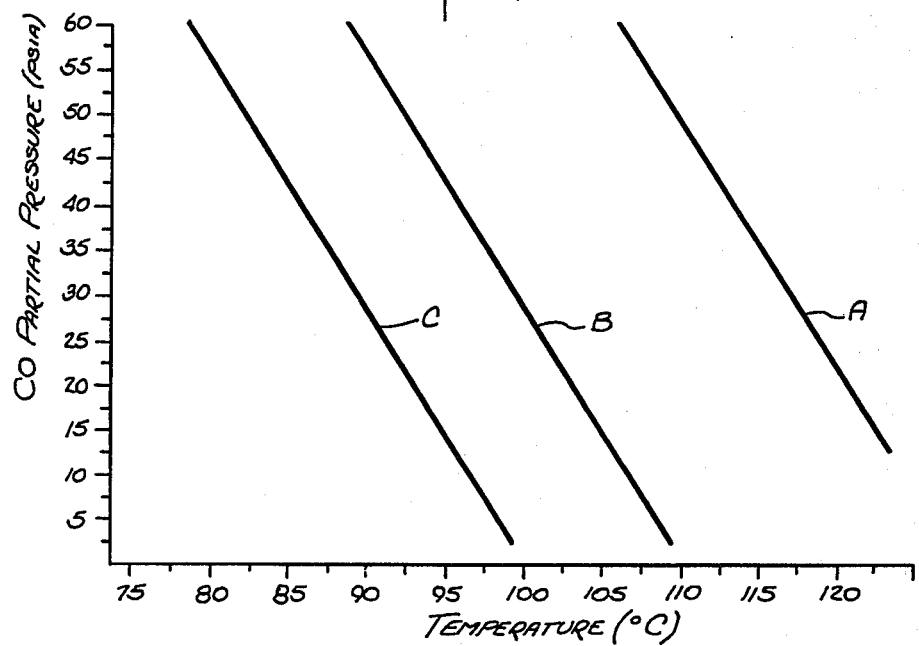
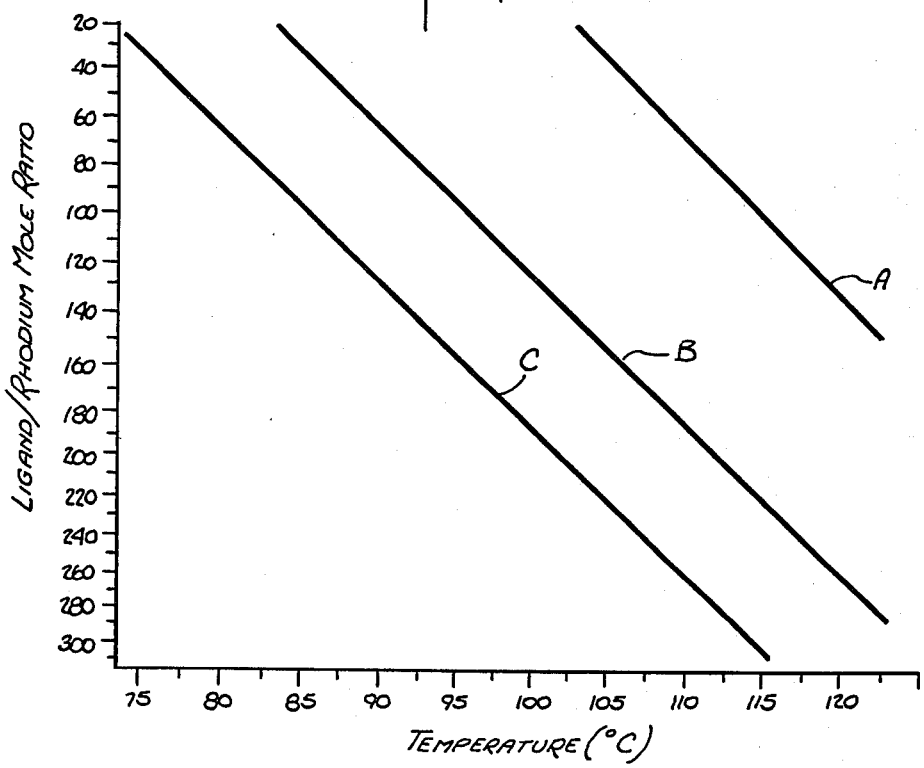

HYDROFORMYLATION PROCESS

This application is a continuation of our prior U.S. application Ser. No. 762,336 filed Jan. 25, 1977.

FIELD OF THE INVENTION

This invention relates to an improved process for the rhodium-catalyzed hydroformylation of olefins, particularly alpha-olefins, to produce the corresponding aldehydes; and more particularly to an improved process for the hydroformylation of alpha-olefins to produce the corresponding aldehydes using rhodium catalysts whose stability is improved by minimizing the intrinsic deactivation of the catalysts which occurs under hydroformylation conditions.

BACKGROUND OF THE INVENTION

Processes for forming an aldehyde by the reaction of an olefin with carbon monoxide and hydrogen have been known as hydroformylation processes or oxo processes. For many years, all commercial hydroformylation reactions employed cobalt carbonyl catalysts which required relatively high pressures (often on the order of 100 atmospheres or higher) to maintain catalyst stability.

U.S. Pat. No. 3,527,809, issued Sept. 8, 1970, to R. L. Pruett and J. A. Smith, discloses a significantly new hydroformylation process whereby alpha-olefins are hydroformylated with carbon monoxide and hydrogen to produce aldehydes in high yields at low temperatures and pressures, where the normal to iso-(or branched-chain) aldehyde isomer ratio of the product aldehydes is high. This process employs certain rhodium complex catalysts and operates under defined reaction conditions to accomplish the olefin hydroformylation. Since this new process operates at significantly lower pressures than required theretofore in the prior art, substantial advantages were realized including lower initial capital investment and lower operating costs. Further, the more desirable straight-chain aldehyde isomer could be produced in high yields.

The hydroformylation process set forth in the Pruett and Smith patent noted above includes the following essential reaction conditions:

(1) A rhodium complex catalyst which is a complex combination of rhodium with carbon monoxide and a triorganophosphorus ligand. The term "complex" means a coordination compound formed by the union of one or more electronically rich molecules or atoms capable of independent existence with one or more electronically poor molecules or atoms, each of which is also capable of independent existence. Triorganophosphorus ligands whose phosphorus atom has one available or unshared pair of electrons are capable of forming a coordinate bond with rhodium.

(2) An alpha-olefin feed of alpha-olefinic compounds characterized by a terminal ethylenic carbon-to-carbon bond such as a vinyl group $CH_2=CH-$. They may be straight chain or branched chain and may contain groups or substituents which do not essentially interfere with the hydroformylation reaction, and they may also contain more than one ethylenic bond. Propylene is an example of a preferred alpha-olefin.

(3) A triorganophosphorus ligand such as a triarylphosphine. Desirably each organo moiety in the ligand does not exceed 18 carbon atoms. The triarylphosphines are the preferred ligands, an example of which is triphenylphosphine.

(4) A concentration of the triorganophosphorus ligand in the reaction mixture which is sufficient to provide at least two, and preferably at least 5, moles of free ligand per mole of rhodium metal, over and above the ligand complexed with or tied to the rhodium atom.

(5) A temperature of from about 50° to about 145° C., preferably from about 60° to about 125° C.

(6) A total hydrogen and carbon monoxide pressure which is less than 450 pounds per square inch absolute (psia), preferably less than 350 psia.

(7) A maximum partial pressure exerted by carbon monoxide no greater than about 75 percent based on the total pressure of carbon monoxide and hydrogen, preferably less than 50 percent of this total gas pressure.

It is known that, under hydroformylation conditions, some of the product aldehydes may condense to form by-product, high boiling aldehyde condensation products such as aldehyde dimers or trimers U.S. Pat. No. 4,148,830 discloses the use of these high boiling liquid aldehyde condensation products as a reaction solvent for the catalyst. In this process, solvent removal from the catalyst, which may cause catalyst losses, is unnecessary and, in fact, a liquid recycle containing the solvent high boiling aldehyde condensation products and catalyst is fed to the reaction zone from a product recovery zone. It may be necessary to remove a small purge stream to prevent the buildup of such aldehyde condensation products and poisons to the reaction to excessive levels of concentration.

More specifically, as pointed out in said U.S. Pat. No. 4,148,830, some of the aldehyde product is involved in various reactions as depicted below using n-butyraldehyde as an illustration:

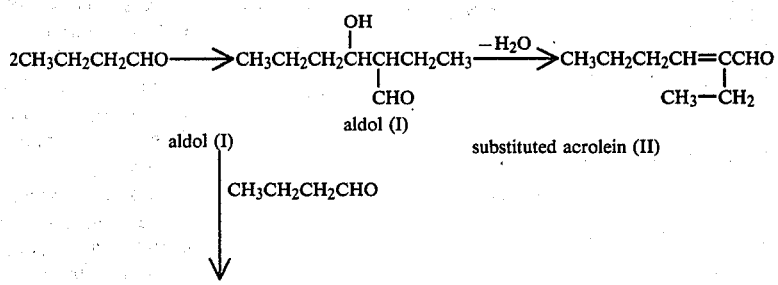

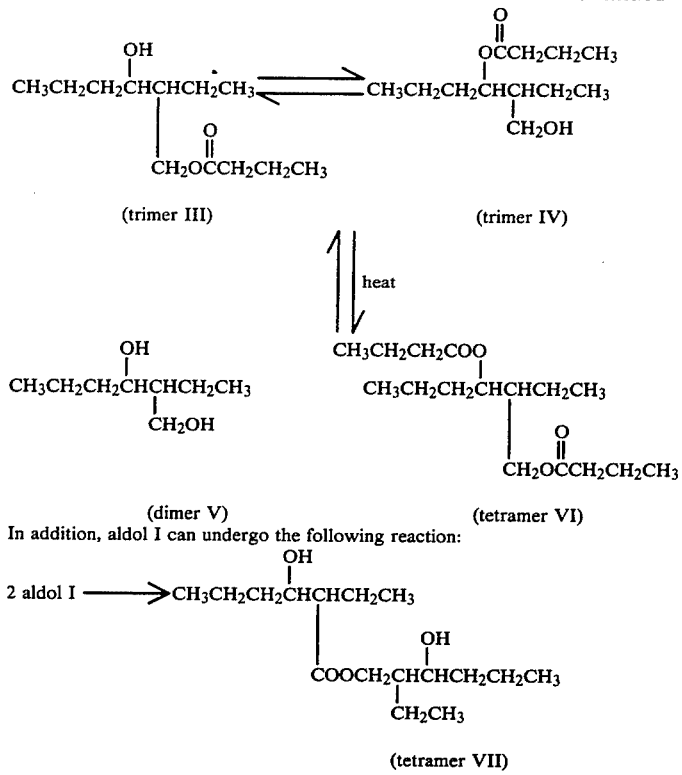

(trimer III) (trimer IV)

(dimer V) (tetramer VI)

In addition, aldol I can undergo the following reaction:

$$2 \text{ aldol I} \longrightarrow \underset{\underset{\underset{CH_2CH_3}{|}}{\underset{COOCH_2CHCH_2CH_2CH_3}{|}}}{\overset{\overset{OH}{|}}{CH_3CH_2CH_2CHCHCH_2CH_3}}$$

(tetramer VII)

The names is parentheses in the afore-illustrated equations, aldol I, substituted acrolein II, trimer III, trimer IV, dimer V, tetramer VI, and tetramer VII, are for convenience only. Aldol I is formed by an aldol condensation; trimer III and tetramer VII are formed via Tischenko reactions; trimer IV by a transesterification reaction; dimer V and tetramer VI by a dismutation reaction. Principal condensation products are trimer III, trimer IV, and tetramer VII, with lesser amounts of the other products being present. Such condensation products, therefore, contain substantial quantities of hydroxylic compounds as witnessed, for example, by trimers III and IV and tetramer VII.

Similar condensation products are produced by self-condensation of iso-butyraldehyde and a further range of compounds is formed by condensation of one molecule of normal butyraldehyde with one molecule of iso-butyraldehyde. Since a molecule of normal butyraldehyde can aldolize by reaction with a molecule of iso-butyraldehyde in two different ways to form two different aldols VIII and IX, a total of four possible aldols can be produced by condensation reactions of a normal/iso mixture of butyraldehydes.

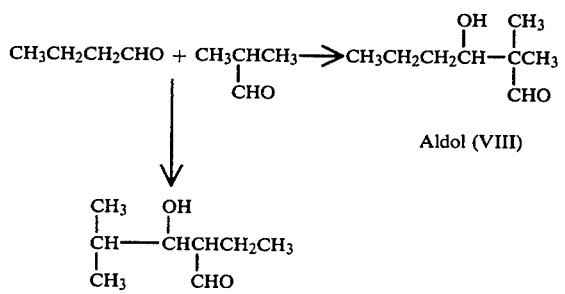

Aldol (VIII)

Aldol I can undergo further condensation with isobutyraldehyde to form a trimer isomeric with trimer III and aldols VIII and IX and the corresponding aldol X produced by self-condensation of two molecules of isobutyraldehyde can undergo further reaction with either normal or isobutyraldehyde to form corresponding isomeric trimers. These trimers can react further analogously to trimer III so that a complex mixture of condensation products is formed.

Commonly-assigned, copending U.S. application Ser. No. 674,823, filed Apr. 8, 1976, discloses a liquid phase hydroformylation reaction using a rhodium complex catalyst, wherein aldehyde reaction products and some of their higher boiling condensation products are removed in vapor form from the catalyst containing liquid body (or solution) at the reaction temperature and pressure. The aldehyde reaction products and the condensation products are condensed out of the off gas from the reaction vessel in a product recovery zone and the unreacted starting materials (e.g., carbon monoxide, hydrogen and/or alpha-olefin) in the vapor phase from the product recovery zone are recycled to the reaction zone. Furthermore, by recycling gas from the product recovery zone coupled with make-up starting materials to the reaction zone in sufficient amounts, it is possible, using a $C_2$ to $C_5$ olefin as the alpha-olefin starting material, to achieve a mass balance in the liquid body in the reactor and thereby remove from the reaction zone at a rate at least as great as their rate of formation essentially all the higher boiling condensation products resulting from self-condensation of the aldehyde product.

More specifically, according to the above latter application, a process for the production of an aldehyde containing from 3 to 6 carbon atoms is disclosed which comprises passing an alpha-olefin containing from 2 to 5 carbon atoms together with hydrogen and carbon monoxide at a prescribed temperature and pressure through a reaction zone containing the rhodium complex catalyst dissolved in a liquid body, continuously removing a vapor phase from the reaction zone, passing the vapor phase to a product separation zone, separating a liquid aldehyde containing product in the product separation zone by condensation from the gaseous unreacted starting materials, and recycling the gaseous unreacted starting materials from the product separation zone to the reaction zone. Preferably, the gaseous unreacted starting materials plus make-up starting materials are recycled at a rate at least as great as that required to maintain a mass balance in the reaction zone.

It is known in the prior art that rhodium hydroformylation catalysts, such as hydrido carbonyl tris(triphenylphosphine)rhodium, are deactivated by certain extrinsic poisons which may be present in any of the gases fed to the reaction mixture. See, for example, G. Falbe, "Carbon Monoxide in Organic Synthesis", Springer-Verleg, New York, 1970. These poisons (X), termed virulent poisons, are derived from materials such as sulfur-containing compounds (e.g., $H_2S$, COS, etc.), halogen-containing compounds (e.g., HCl, etc.), cyano-containing compounds (e.g., HCN, etc.), and the like, and can form Rh-X bonds which are not broken under mild hydroformylation conditions. If one removes such poisons from the materials fed to the reaction mixture, to below 1 part per million (ppm), one would expect therefore that no such deactivation of the catalyst would occur. However, it has been found that such is not the case. For example, when very clean gases (<1 ppm extrinsic poisons) were used in the hydroformylation of propylene and the gas recycle technique discussed above was employed, under the following conditions:

| | |
|---|---|
| temperature (°C.) | 100 |
| CO partial pressure (psia) | 36 |
| $H_2$ partial pressure (psia) | 75 |
| olefin partial pressure (psia) | 40 |
| ligand/rhodium mole ratio | 94 | the catalyst activity decreased at a rate of 3% per day (based on the original activity of the fresh catalyst). It appears therefore that even the substantially complete removal of extrinsic piosons does not prevent such catalyst deactivation, which we shall term intrinsic catalyst deactivation.

The prior art, to our knowledge, does not propose a solution to this problem of intrinsic deactivation of rhodium hydroformylation catalysts, nor does it even recognize the reasons for the same.

Japanese Patent Application No. Sho-49-85523 discloses that in a process of hydroformylating olefins using a rhodium-tertiary phosphine catalyst, wherein catalyst-containing solution separated from the reaction product is recycled to the reaction and reused, high-boiling by-products and complexes which do not have any or have a reduced catalytic activity formed by a change in the structure of the rhodium-tertiary phosphine complex itself and by the action of impurities such as oxygen, halogens, sulfur, etc., contained to a small extent in the starting materials, accumulate gradually in the catalyst solution. The patent states that in order to carry out the hydroformylation reaction continuously and in a stable manner, the catalytic activity of the recycle catalyst solution is maintained at a constant level by supplying fresh catalyst to the recycled solution and at the same time removing a part of the recycled catalyst solution. With this procedure, the rhodium removed from the catalyst solution must be recovered due to the cost of the rhodium. However, processes for recovering rhodium from solution are complicated and the resulting hydroformylation reaction becomes economically disadvantageous. This patent proposes a process for reactivating the inactivated catalyst by treating the catalyst solution with carbon dioxide.

W. Strohmeier and A. Kuhn, in *Journal of Organometallic Chemistry*, 110, 265–270 (1976), discussed the hydroformylation of 1-hexene under mild conditions (40° C., 1 atmosphere) using $HRhCO[P(C_6H_5)_3]_3$ as a catalyst in the absence of a solvent, and noted a deactivation of the catalyst. The effects of $P(C_6H_5)_3$ addition and CO partial pressure on the conversion are studied and it is stated that optimum conversion (at a normal:iso aldehyde ratio of 99:1) is obtained with a $H_2$:CO ratio of 1:1 and with the addition of $P(C_6H_5)_3$. The authors do not state the cause of the observed deactivation nor do they propose a solution.

G. Wilkinson and his colleagues noted a deactivation of the catalyst $HRhCO[P(C_6H_5)_3]_3$ when used in the hydrogenation of alkenes [M. Yagupsky et al, *Journal of the Chemical Society (A)*, 1970, pages 937–941], and in fact noted that in a hydroformylation process no loss in activity of this catalyst has been noted "even after many cycles" (see page 937), citing C. K. Brown and G. Wilkinson, *Tetrahedron Letters*, 1969, 1725.

U.S. Pat. No. 3,555,098 discloses a process for avoiding the deactivation of a hydrocarbonylation catalyst by treating all or a portion of a liquid recycle reaction medium with an aqueous solution. It is disclosed that this treatment removes carboxylic acid byproducts (formed by oxidation of the product aldehydes/alcohols) and prevents the deactivation of the reaction medium.

We have found that the aforementioned intrinsic deactivation of rhodium catalysts under hydroformylation conditions is caused by the combination of the effects of temperature, the partial pressures of both carbon monoxide and hydrogen and the phosphine ligand:rhodium mole ratio. It has further been determined that this deactivation produces non-catalytically active material. It would be desirable to minimize or eliminate this intrinsic deactivation problem in order to achieve a truly optimum commercial operation; that is, a rhodium-catalyzed hydroformylation reaction which produces the desired product at commercially attractive conversion rates at conditions such that the catalyst remains active over a prolonged period of time.

SUMMARY OF THE INVENTION

The present invention comprises a rhodium-catalyzed hydroformylation process involving the controlling and correlating of reaction conditions to minimize or substantially eliminate the intrinsic deactivation of the rhodium complex catalyst. Deactivation is minimized or substantially prevented and a stable rhodium complex catalyst is provided by the careful control and correlation of the combination of at least the carbon monoxide partial pressure, the temperature and the free triorganophosphorus ligand:catalytically-active rhodium mole ratio. Generally, operation at low carbon monoxide partial pressure, low temperature and high free triorganophosphorus:catalytically-active rhodium mole ratio inhibits the deactivation of the rhodium complex catalyst. By correlating these three parameters, which in combination are related to catalyst stability, and from which the catalyst stability can be predicted, the intrinsic deactivation of the rhodium complex catalyst can be minimized or substantially prevented.

DESCRIPTION OF THE PREFERRED EMBODIMENTS

Figure 1:
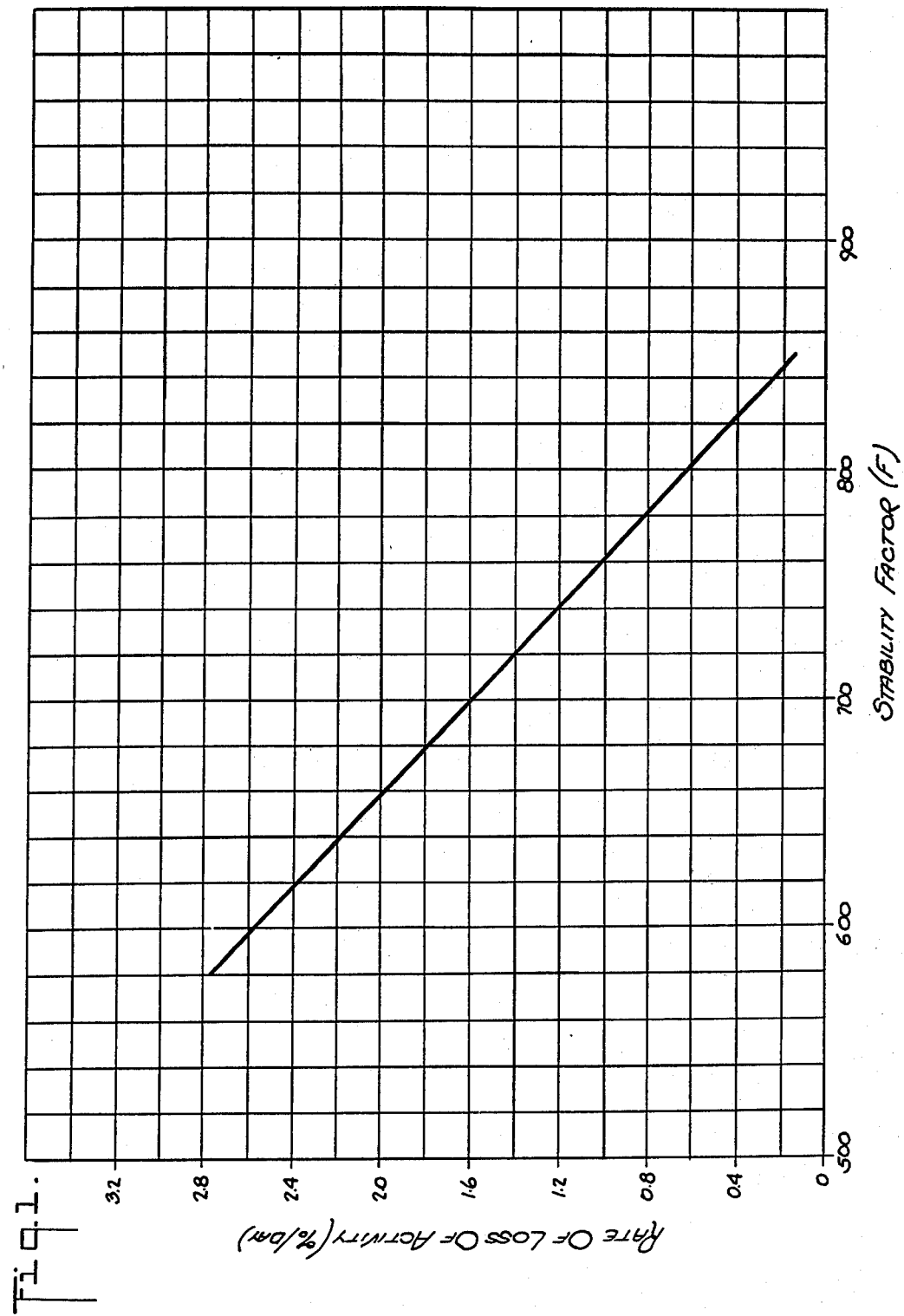

In its broadest sense, the present invention comprises a rhodium-catalyzed hydroformylation process for producing aldehydes from alpha-olefins including the steps of reacting the olefin with hydrogen and carbon monoxide in the presence of a rhodium complex catalyst consisting essentially of rhodium complexed with carbon monoxide and a triarylphosphine, under certain defined reaction conditions, as follows:

(1) a temperature of from about 90° to about 130° C.;
(2) a total gas pressure of hydrogen, carbon monoxide and alpha-olefin of less than about 400 psia;
(3) a carbon monoxide partial pressure of less than about 55 psia;
(4) a hydrogen partial pressure of less than about 200 psia;
(5) at least about 100 moles of free triarylphosphine ligand for each mole of catalytically active rhodium metal present in the rhodium complex catalyst; and selectively correlating the partial pressure of carbon monoxide, the temperature and the free triarylphosphine: catalytically active rhodium mole ratio to limit the rhodium complex catalyst deactivation to a maximum determined percent loss in activity per day, based on the initial activity of the fresh catalyst. It has been found that the combination of these three parameters exerts a synergistic effect on the stability of the catalyst. By "catalytically active rhodium" is meant the rhodium metal in the rhodium complex catalyst which has not been deactivated. The amount of rhodium in the reaction zone which is catalytically active may be determined at any given time during the reaction by comparing the conversion rate to product based on such catalyst to the conversion rate obtained using fresh catalyst.

The manner in which the carbon monoxide partial pressure, temperature and free triarylphosphine:-catalytically active rhodium mole ratio should be controlled or correlated to thus limit the deactivation of the catalyst is illustrated as follows.

As an example, for the triarylphosphine ligand triphenylphosphine, the specific relationship between these three parameters and catalyst stability is defined by the formula:

$$F = \frac{1000}{1 + e^Y}$$

where
F = stability factor
e = Naperian log base (i.e., 2.718281828)
$y = K_1 + K_2T + K_3P + K_4(L/Rh)$
T = reaction temperature (°C.)
P = partial pressure of CO (psia)
L/Rh = free triarylphosphine:catalytically active rhodium mole ratio
$K_1 = -8.1126$
$K_2 = 0.07919$
$K_3 = 0.0278$
$K_4 = -0.01155$ In the above formula, and in practice, to determine the stability factor of a catalyst under actual hydroformylation conditions in the presence of an olefin, an olefin response factor must be employed to obtain the actual stability factor. In this connection it has been found that olefins generally enhance the stability of the catalyst. This will be more fully discussed below.

The above relationship is substantially the same for other triarylphosphines, except that the constants $K_1$, $K_2$, $K_3$ and $K_4$ may be different. Those skilled in the art can determine the specific constants for other triarylphosphines with a minimum amount of experimentation, such as by repeating Examples 1-10 below with other triarylphosphines.

As can be understood by referring to the above formula, for given conditions of reaction temperature, carbon monoxide partial pressure and free triarylphosphine:catalytically active rhodium mole ratio, the stability factor F can be determined. The stability factor F exhibits a predictive relationship with the rate at which the rhodium complex catalyst is deactivated under hydroformylation conditions. This relationship is illustrated by FIG. 1 of the drawings which shows the variation in the stability factor F for different rates of catalyst activity losses for the triarylphosphine triphenylphosphine. This drawing indicates that the rate of activity loss decreases in a substantially linear relationship with increasing values of the stability factor F. The determination of the maximum permissible rate of activity loss of the catalyst must ultimately be based to a large extent on the economics of the process, including predominantly the cost of replacing spent or deactivated catalyst and also the value of the products, etc. For purposes of discussion only, if it is assumed that the maximum acceptable rate of activity loss of the catalyst is 0.75 percent per day, from FIG. 1 it is seen that the corresponding minimum stability factor F is about 770. The above equation can then be employed to determine the reaction conditions which will provide this minimum necessary stability factor F and, as a result this maximum acceptable rate of loss of catalyst activity.

Figure 4:
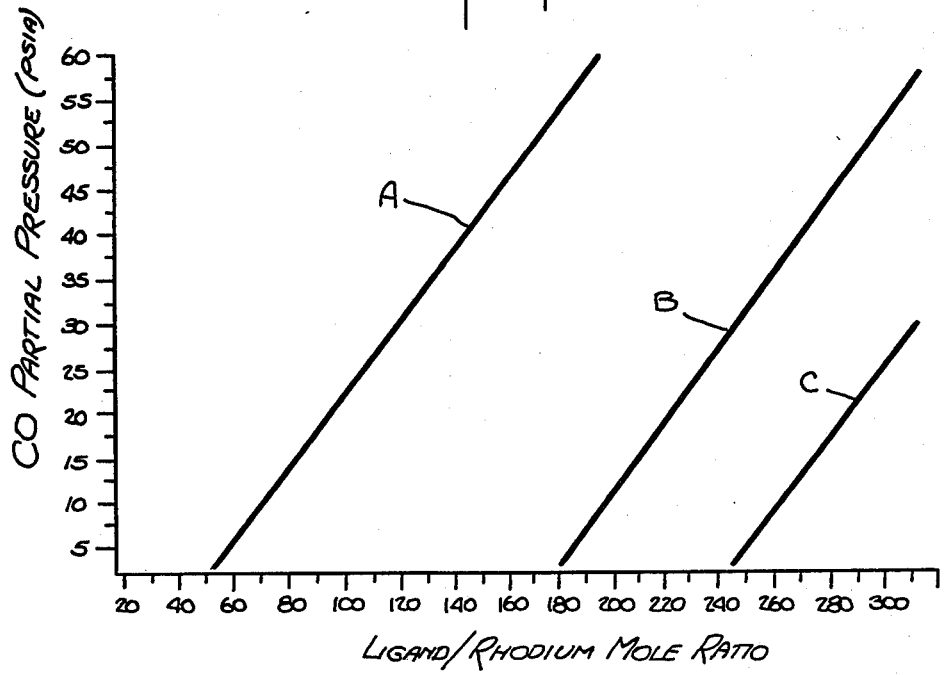

Inasmuch as the above equation has three variables, it can better be understood by reference to FIGS. 2, 3 and 4 of the drawings which show the effect on the stability factor F of varying two of these three variables, the other being held constant. More specifically, FIGS. 2, 3 and 4 illustrate the effect of these three variables on the stability factor F for the olefin propylene, and for ease of description, the following discussion will be limited to propylene as the olefin. However, it is to be understood that a similar relationship exists for other olefins which could be similarly illustrated as in FIGS. 2, 3 and 4.

Referring to FIG. 2 the values represented there were obtained by calculating the stability factor F in the hydroformylation of propylene at a constant free triarylphosphine:catalytically-active rhodium mole ratio of 170:1 (the specific triarylphosphine being triphenylphosphine) and at varying temperatures and carbon monoxide partial pressures. Lines A, B and C are the areas along which the stability factor F is about 500, 800 and 900, respectively. As is apparent from FIG. 2, the stability factor F is highest at low carbon monoxide partial pressures and low temperatures, at a fixed free triarylphosphine:catalytically-active rhodium mole ratio.

FIG. 3 illustrates the relationship between the stability factor F and varying temperatures and free triarylphosphine:catalytically-active rhodium mole ratios (triarylphosphine = triphenylphosphine), with a constant carbon monoxide partial pressure of 25 psia for the hydroformylation of propylene. Lines A, B and C are the areas along which the stability factor F is about 500, 800 and 900, respectively. As is apparent from FIG. 3, the stability factor F is highest at low temperatures and high free triarylphosphine:catalytically-active rhodium mole ratios, at a fixed carbon monoxide partial pressure.

FIG. 4 illustrates the relationship between the stability factor F and varying carbon monoxide partial pressures and free triarylphosphine:catalytically-active rhodium mole ratios (triarylphosphine=triphenylphosphine), with a constant reaction temperature of 110° C. for the hydroformylation of propylene. Lines A, B and C are the areas along which the stability factor F is about 500, 800 and 900, respectively. As is apparent from FIG. 4, the stability factor F is highest at high free triarylphosphine:catalytically-active rhodium mole ratios and low carbon monoxide partial pressures, at a fixed temperature.

It should be understood that FIGS. 2, 3 and 4 of the drawings are intended to be representative only. For example, referring to FIG. 4, if a different fixed constant temperature was employed, the plotted values of stability factor F would be different. The same holds for FIGS. 2 and 3 if different fixed values of the free triarylphosphine:catalytically-active rhodium mole ratio and carbon monoxide partial pressure were employed. In effect, each of FIGS. 2, 3 and 4 represents a single plane of the three-dimensional relationship which exists between the stability factor F and the conditions temperature, carbon monoxide partial pressure and free triarylphosphine:catalytically-active rhodium mole ratio, the plane of course being the same as the plane of the three-dimensional plot which intersects the selected value of the fixed variable in each case. These two-dimensional representations have been presented for ease of description only.

In summary therefore, the conditions of temperature, carbon monoxide partial pressure and free triarylphosphine:catalytically-active rhodium mole ratio which are controlled and correlated to obtain minimum catalyst deactivation are determined as follows. The threshold determination is of a maximum acceptable rate of loss of catalyst activity. With this value and using, for example, the relationship illustrated by FIG. 1, the minimum stability factor F can be determined. The above equation is then solved to determine the values of the three variables which are adjusted to obtain this minimum stability factor F, and in this connection, representations such as FIGS. 2, 3 and 4 are helpful in ascertaining specific conditions which will provide a stable catalyst.

For purposes of the present invention, it is believed that a realistic value for the rate of loss of activity of the rhodium complex catalyst, in a commercial operation, is 0.5 percent per day, based on the activity of the fresh catalyst. By the term "activity" is meant, for example, the amount of product produced expressed as gram-moles/liter-hour. Of course, any other standard technique can be employed to determine the relative activity of the catalyst at any given time.

Broadly however, according to the present invention, the maximum loss of activity of the rhodium complex catalyst should be 0.75 percent per day, and highly advantageous results are achieved where the maximum rate of loss of catalyst activity is 0.3 percent per day, both being based upon the activity of the fresh catalyst. It should be understood, however, that in its broadest sense, the present invention is not to be limited to any maximum rate of loss of catalyst activity since this would depend on many different factors, as pointed out above. Rather, the present invention provides a mechanism for obtaining any maximum rate of loss of catalyst activity by the control and correlation of the hydroformylation reaction conditions. Stated conversely, once a maximum acceptable rate of loss of catalyst activity is determined, the present invention provides one skilled in the art with the tools to control and correlate the reaction conditions necessary to obtain catalyst stability. Therefore, the values given above for the maximum rate of loss of catalyst activity should not limit the scope of the present invention since they are provided to teach those skilled in the art how to practice the present invention.

As pointed out above, the presence of the olefin in the hydroformylation reaction enhances the stability of the catalyst; that is, it inhibits the deactivation caused by the combination of carbon monoxide, hydrogen, temperature and ligand/rhodium mole ratio. One can determine the effect of the olefin upon the stability factor calculation. For example, we have found that in the hydroformylation of propylene, reactions conditions that will provide long-term catalyst stability (i.e., a low rate of loss of catalyst activity) give a stability factor F, determined from FIG. 1 with the observed rate of loss of catalyst activity, of about 850. However, by using these conditions and the above formula, a stability factor F of about 870 is calculated. It is only necessary to then make the appropriate modification in the above equation to include the effect of the propylene on the stability factor. Similar data can easily be obtained for other olefins, and the necessary modifications can be made in the above formula to determine the actual reaction conditions which should be employed to obtain the benefits of the present invention; i.e. long-term catalyst stability.

The process of the present invention is expected to be useful for the hydroformylation of alpha-olefins having up to 20 carbon atoms. The process of the present invention is particularly useful for the hydroformylation of alpha-olefins having from 2 to 5 carbon atoms, including ethylene, propylene, 1-butene, 1-pentene and the like, and therefore this constitutes a preferred embodiment. The process of the present invention is especially useful for the hydroformylation of propylene to form butyraldehydes having a high normal to iso ratio; i.e. the butyraldehyde which predominates in the product is the normal butyraldehyde, and hence this presently constitutes the most preferred embodiment. The alpha-olefins used in the process of the invention may be straight-chain or branched-chain and may contain groups or substituents which do not essentially interfere with the course of the hydroformylation reaction.

The rhodium complex catalyst used in the process of the invention consists essentially of rhodium complexed with carbon monoxide and a triarylphosphine ligand. The terminology "consists essentially of" is not meant to exclude, bur rather to include, hydrogen complexed with the rhodium, in addition to carbon monoxide and a triarylphosphine. However, this language is meant to exclude other materials in amounts which poison or deactivate the catalyst. Illustrative triarylphosphine ligands are triphenylphosphine, trinaphthylphosphine, tritolylphosphine, tri(p-biphenyl)phosphine, tri(p-methoxyphenyl)phosphine, p-N,N-dimethylaminophenyl bis-phenylphosphine, and the like. The most desirable catalyst has no rhodium-bound halogen such as chlorine and like species, and contains hydrogen, carbon monoxide and triarylphosphine complexed with rhodium metal to produce a catalyst which is normally soluble in liquids which may be used as a solvent in the reaction and which is stable under the conditions of reaction determined and controlled according to the invention. Triphenylphosphine is the preferred ligand, and as pointed out previously, an excess of the triarylphosphine ligand is present in the reaction medium. Higher mole ratios of free triarylphosphine:catalytically-active rhodium metal favor the stability of the catalyst. By "free" triarylphosphine is meant the triarylphosphine that is not tied to or complexed with the rhodium atom in the active complex catalyst. The theory of how such ligands complex with the rhodium is given in said U.S. Pat. No. 3,527,809.

According to the present invention, the amount of free triarylphosphine in the reaction medium is sufficient to provide a free triarylphosphine:catalytically active rhodium mole ratio of at least 100. Advantageous and preferred results are achieved when this mole ratio is at least 150. The upper limit of this mole ratio does not appear to be particularly critical and would be dictated largely by commercial and economic considerations. Of course, the amount of free triarylphosphine depends on the necessary stability factor F which in turn is related to the free triarylphosphine:catalytically active rhodium mole ratio by the above equation.

The rhodium complex catalyst may be formed by methods known in the art. For example, a preformed stable crystalline solid of rhodium hydridocarbonyl-tris(triphenylphosphine), $RhH(CO)[P(C_6H_5)_3]_3$, may be introduced into the reaction medium. This material may be formed, for example, by a method disclosed in Brown, et al., *Journal of the Chemical Society*, 1970, pages 2753–2764. Alternatively, a rhodium catalyst precursor such as $Rh_2O_3$, $Rh_4(CO)_{12}$, or $Rh_6(CO)_{16}$ and the like, may be introduced into the reaction medium. In a preferred embodiment, rhodium carbonyl triphenylphosphine acetylacetonate or rhodium dicarbonyl acetylacetonate are employed. In any event, the active rhodium complex catalyst is formed in the reaction medium under the conditions of hydroformylation.

The amount of catalyst present in the reaction medium should be as a minimum that amount which is necessary to catalyze the hydroformylation of the alpha-olefin to form the product aldehydes. Generally, the rhodium concentration in the reaction medium can range from about 25 ppm to about 1200 ppm, preferably about 50 ppm to about 400 ppm, of catalytically active rhodium calculated as the free metal. The triarylphosphine ligand is present in sufficient quantities to form the catalyst complex and to provide the above minimum number of moles of free triarylphosphine per mole of catalytically active rhodium metal. Generally, the triarylphosphine ligand is present in the reaction medium in an amount of from about 0.5 percent to about 30 percent by weight based on the weight of the total reaction medium, and in an amount sufficient to provide the desired number of moles of free triarylphosphine ligand per mole of catalytically active rhodium.

The amount of olefin fed to the reaction mixture depends on several factors, such as the size of the reactor, the temperature of reaction, the total pressure, the amount of catalyst, etc. In general, the higher the olefin concentration is in the reaction medium, the lower usually will be the catalyst concentration that can be used to achieve a given conversion rate to aldehyde products in a given size of reactor. Since partial pressures and concentration are related, the use of higher olefin partial pressure leads to an increased proportion of the olefin in the product stream leaving the reaction mixture. Further, since some amount of saturated hydrocarbon may be formed by hydrogenation of the olefin, it may be necessary to purge part of the product gas stream in order to remove this saturated product before any recycle to the reaction zone, and this would be a source of loss for the unreacted olefin contained in the product gas stream. Hence, it is necessary to balance the economic value of the olefin lost in such a purge stream against the economic savings associated with lower catalyst concentration.

The temperature of reaction, as noted above, may vary from about 90° to about 130° C., with the lower temperatures favoring catalyst stability. The particular temperature employed in the reaction will of course depend upon the necessary stability factor F, since temperature is interrelated with the carbon monoxide partial pressure and the free triarylphosphine:catalytically active rhodium mole ratio by the above equation. Generally, by controlling the temperature as taught above to obtain the necessary stability, within the foregoing temperature range, the advantages of the present invention can be attained. It is preferred for the process of the invention to operate at a temperature of from 90° to 120° C.

A substantial advantage of the process disclosed in U.S. Pat. No. 3,527,809 is the low total pressure of hydrogen and carbon monoxide required to conduct the hydroformylation reaction. The process of the present invention operates at a total pressure of carbon monoxide, hydrogen and olefin of less than 400 psia, preferably less than 350 psia. The minimum total pressure is not particularly critical and is limited predominantly only by the amount of reaction gases necessary to obtain the desired rate of reaction.

The make-up gases fed to the reaction medium would include the olefin, carbon monoxide and hydrogen, usually. As pointed out previously, extrinsic poisons such as sulfur and sulfur-containing compounds, as well as halogens and halogencontaining compounds, and the like, should be excluded from the make-up gases, since it is known that such materials poison the catalyst and can deactivate the catalyst rather rapidly. Hence, it is desirable to reduce the amount of such poisons in all gases fed to the reaction. Of course, the amount of such poisons that can be tolerated is determined by the maximum acceptable rate of loss of activity of the catalyst, discussed above. If it is possible to permit some small amount of such poisons and still obtain a catalyst of desired stability, then such small amounts can be tolerated. It is generally desirable to reduce the amounts of such poisons in the make-up gases to below one part per million. This can be accomplished by methods known in the art.

The partial pressure of hydrogen in the reaction mixture is an important part of the present invention. Although it is not per se reflected in the formula set forth above, the effect of the hydrogen partial pressure is included in the constant $K_1$ in the formula. Hydrogen does have some effect on catalyst deactivation. Accordingly, according to the process of the invention, the partial pressure of hydrogen should be less than about 200 psia, and preferably it should range from about 60 to about 160 psia. Of course, the particular value will be determined depending upon the necessary stability factor and the relationship of the hydrogen partial pressure to the carbon monoxide partial pressure, as discussed below.

The partial pressure of carbon monoxide has a significant effect on the stability of the catalyst, and should generally be less than about 55 psia. Of course, the particular partial pressure employed will depend upon the necessary stability factor. As a general rule, lower carbon monoxide partial pressures provide more stable catalysts. It is preferred according to the process of the invention that the partial pressure of carbon monoxide be from about 2 psia to about 20 psia. The minimum partial pressure of carbon monoxide is not critical in that it is limited predominantly only by the desired rate of reaction and the possibility of olefin hydrogenation occurring.

It is disclosed in U.S. Pat. No. 3,527,809 that the normal to iso aldehyde isomer ratio of the aldehyde products decreases as the partial pressure of carbon monoxide increases relative to the hydrogen partial pressure. Similarly, in the process of the present invention, the partial pressure of carbon monoxide relative to the partial pressure of hydrogen has an effect on the isomer ratio of the product aldehydes. Generally, to obtain the more desirable normal aldehyde isomer, the ratio of partial pressures of hydrogen:carbon monoxide should be at least about 2:1, preferably at least about 8:1. As long as the partial pressures of each of carbon monoxide and hydrogen are controlled within the limits described above, there is no critical maximum ratio of the hydrogen:carbon monoxide partial pressures.

The time of reaction, or residence period of the olefin in the reaction zone, is generally that time which is sufficient to hydroformylate the alpha-ethylenic bond of the alpha-olefin. As a general rule, the residence period in the reaction zone can vary from about several minutes to about several hours in duration and as is apparent, this variable will be influenced, to a certain extent, by the reaction temperature, the choice of alpha-olefin and catalyst, the concentration of free ligand, the total pressure, the partial pressure exerted by carbon monoxide and hydrogen, the conversion rate and other factors. As a general rule, it is desirable to achieve the highest possible conversion rate for the smallest amount of catalyst employed. Of course, the ultimate determination of a conversion rate is influenced by many factors including the economics of the process. A substantial advantage of the present invention is that catalyst deactivation is minimized or substantially prevented while obtaining excellent conversion rates over prolonged periods of time.

It is preferred to effect the process of the invention in a liquid phase in the reaction zone which contains the rhodium complex catalyst and, as a solvent therefore, the higher boiling liquid aldehyde condensation products.

By the term "higher boiling liquid aldehyde condensation products" as used herein is meant the complex mixture of high boiling liquid products which result from the condensation reactions of some of the aldehyde products of the process of the invention, as illustrated hereinabove. Such condensation products can be preformed or produced in situ in the present process. The rhodium complex catalyst is soluble in these relatively high boiling liquid aldehyde condensation products while exhibiting excellent stability over extended periods of continuous hydroformylation. In a preferred form of the process of the invention the higher boiling liquid aldehyde condensation products to be used as solvents are preformed prior to introduction into the reaction zone and the start-up of the process. It is also preferred to maintain the condensation products illustrated by acrolein II above, and its isomers, at low concentrations in the reaction medium, such as below about 5 weight percent and lower based on the total weight of the reaction medium.

These higher boiling liquid aldehyde condensation products are more fully described, and methods for preparing the same are more fully described, U.S. Pat. No. 4,148,830, and reference can be made to this patent for a more detailed description.

It is also preferred according to the process of the invention to employ the gas recycle technique described in said commonly-assigned, copending U.S. Application Ser. No. 674,823, filed Apr. 8, 1976. This gas recycle process is broadly described above. If the aforementioned higher boiling liquid aldehyde condensation products are employed as the solvent, the liquid body in the reaction zone will comprise a homogeneous mixture containing the soluble catalyst, the free triarylphosphine ligand, the solvent, the product aldehydes and the reactants, alpha-olefin, carbon monoxide and hydrogen.

The relative proportion of each reaction product in solution is controlled by the amount of gas passing through the solution. Increasing this amount decreases the equilibrium aldehyde concentration and increases the rate of by-product removal from solution. The by-products include the higher boiling liquid aldehyde condensation products. The decreased aldehyde concentration leads to a reduction in the rate of formation of the by-products.

The dual effect of increased removal rate and decreased formation rate means that the mass balance in by-products in the reactor is very sensitive to the amount of gas passing through the liquid body. The gas cycle typically includes make-up quantities of hydrogen, carbon monoxide and alpha-olefin. However, the most meaningful factor is the amount of recycle gas returned to the liquid body since this determines the degree of reaction, the amount of product formed and the amount of by-product (as a consequence) removed.

Operation of the hydroformylation reaction with a given flow rate of olefin and synthesis gas (i.e., carbon monoxide and hydrogen) and with a total low amount of gas recycle less than a critical threshold rate results in a high equilibrium aldehyde concentration in solution and hence, the high by-product formation rates.

The rate of removal of by-products in the vapor phase effluent from the reaction zone (liquid body) under such conditions will be low because the low vapor phase effluent flow rate from the reaction zone can only result in a relatively low rate of carry-over of by-products. The net effect is a build-up of by-products in the liquid body solution causing an increase in the solution volume with a consequent loss of catalyst productivity. A purge must therefore be taken from the solution when the hydroformylation process is operated under such low gas flow rate conditions in order to remove by-products and hence maintain a mass balance over the reaction zone.

If however, the gas flow rate through the reaction zone is increased by increasing the gas recycle rate the solution aldehyde content falls, the by-product formation rate is decreased and by-product removal rate in the vapor phase effluent from the reaction zone is increased. The net effect of this change is to increase the proportion of the by-products removed with vapor phase effluent from the reaction zone. Increasing the gas flow rate through the reaction zone still further by a further increase in the gas recycle rate leads to a situation in which by-products are removed in the vapor phase effluent from the reaction zone at the same rate as they are formed, thus establishing a mass balance over the reaction zone. This is the critical threshold gas recycle rate which is the preferred minimum gas recycle rate used in the process of the invention. If the process is operated with a gas recycle rate higher than this threshold gas recycle rate the volume of the liquid body in the reaction zone will tend to decrease and so, at gas recycle rates above the threshold rate, some of the crude aldehyde by-product mixture should be returned to the reaction zone from the product separation zone in order to keep constant the volume of the liquid phase in the reaction zone.

The critical threshold gas recycle flow rate can be found by a process of trial and error for a given olefin and synthesis gas (the mixture of carbon monoxide and hydrogen) feed rate. Operating at recycle rates below the critical threshold rates will increase the volume of the liquid phase with time. Operating at the threshold rate keeps the volume constant. Operating above the threshold rate decreases the volume. The critical threshold gas recycle rate can be calculated from the vapor pressures at the reaction temperature of the aldehyde or aldehydes and of each of the by-products present.

With the process operating at a gas recycle rate at or greater than the threshold rate, by-products are removed in the gaseous vapors removed from the reaction zone containing the liquid body at the same rate as or faster than they are formed, and thus do not accumulate in the liquid phase in the reaction zone. Under such circumstances, it is unnecessary to purge the liquid body containing the catalyst from the reaction zone in order to remove by-products.

A by-product of the hydroformylation process is the alkane formed by hydrogenation of the alpha-olefin. Thus, for example, in the hydroformylation of propylene a by-product is propane. A purge stream may be taken from the gas recycle stream from the product recovery zone in order to remove propane and prevent its build-up within the reaction system. This purge stream will contain, in addition to unwanted propane, unreacted propylene, any inert gases introduced in the feedstock and a mixture of carbon monoxide and hydrogen. The purge stream can, if desired, be submitted to conventional gas separation techniques, e.g. cryogenic techniques, in order to recover the propylene, or it may be used as a fuel. The composition of the recycle gas is principally hydrogen and propylene. However, if the carbon monoxide is not all consumed in the reaction, the excess carbon monoxide will also be part of the recycle gas. Usually the recycle gas will contain alkane even with purging before recycle.

Figure 5:
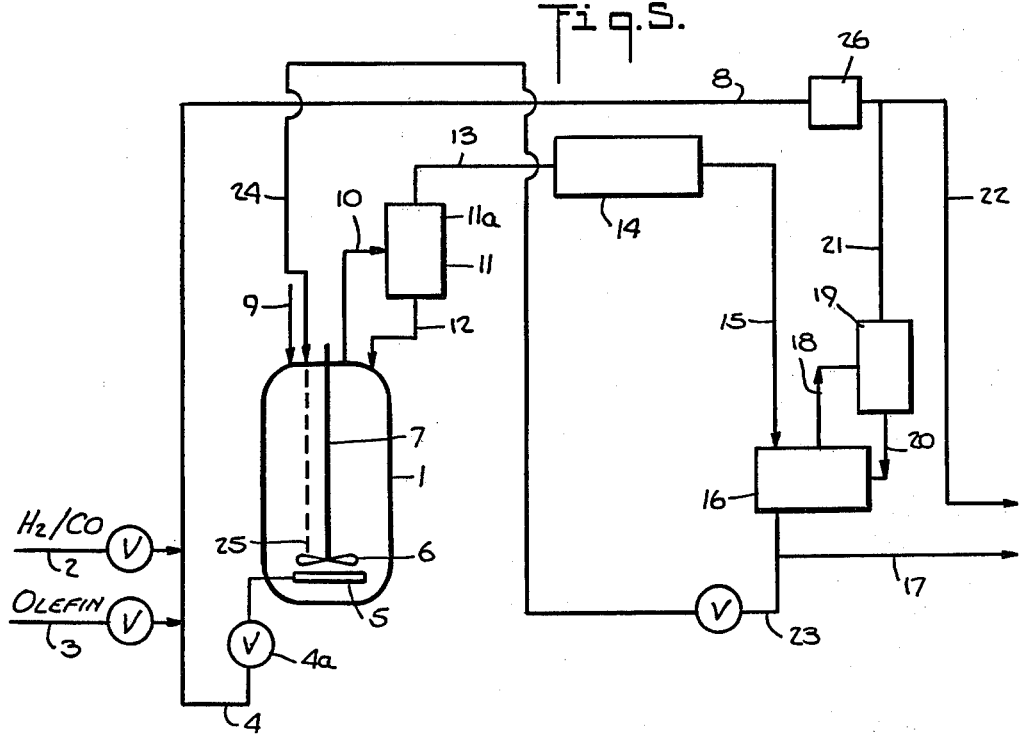

The preferred gas recycle is further illustrated with reference to FIG. 5 of the accompanying drawings which schematically shows a diagramatic flowsheet suitable in practising the preferred recycle process of the invention.

Referring to the drawing, a stainless steel reactor 1 is provided with one or more disc impellers 6 containing perpendicularly mounted blades and rotated by means of shaft 7, by a suitable motor (not shown). Located below the impeller 6 is a circular tubular sparger 5 for feeding the alpha-olefin, and synthesis gas plus the recycle gas. The sparger 5 contains a plurality of holes of sufficient size to provide sufficient gas flow into the liquid body at about the impeller 6 to provide the desired amount of the reactants in the liquid body. The reactor is also provided with a steam jacket (not shown) by means of which the contents of the vessel can be brought up to reaction temperature as start-up and internal cooling coils (not shown).

Vaporous product effluent from the reactor 1 is removed via line 10 to separator 11 where they are passed through a demisting pad 11a therein to return some aldehyde and condensation product and to prevent potential carry-over of catalyst. The reactor effluent is passed by line 13 to a condenser 14 and then through line 15 to catchpot 16 in which the aldehyde product and any by-product can be condensed out of the off gases (effluent). Condensed aldehyde and by-products are removed from the catchpot 16 by line 17. Gaseous materials are passed via line 18 to separator 19 containing a demisting pad and recycle line 20. Recycle gases are removed by line 21 to line 8 from which a purge through line 22 is pulled to control saturated hydrocarbon content and maintain desirable system pressure. The remaining and major proportion of the gases can be recycled via line 8 to line 4 into which is fed make-up reactant feeds through lines 2 and 3. The combined total of reactants are fed to the reactor 1. Compressor 26 aids in transporting the recycle gases.

Fresh catalyst solution can be added to the reactor 1 by line 9. The single reactor 1 can of course, be replaced by a plurality of reactors.

The crude aldehyde product of line 17 can be treated by conventional distillation to separate the various aldehydes and the condensation products. A portion of the crude can be recycled to reactor 1 through line 23 and fed as indicated by broken-line 25 to a point above impeller 6 for the purpose of maintaining the liquid level in reactor 1 if such is required.

As pointed out above, the most preferred embodiment of the present invention is the hydroformylation of the alpha-olefin propylene. The stability of the rhodium complex catalyst is enhanced by the techniques of the invention, and in the case of propylene, the reaction is controlled by the process of the invention within the following conditions:

temperature: about 90° to about 120° C.
total gas pressure of hydrogen, carbon monoxide and propylene: less than about 350 psia
carbon monoxide partial pressure: about 2 to about 20 psia
hydrogen partial pressure: about 60 to about 160 psia
triarylphosphine:triphenylphosphine
free triphenylphosphine:catalytically-active rhodium mole ratio: about 150:1 to about 300:1

In the hydroformylation of propylene according to the invention, it has been found, and it is therefore preferred, that the conditions of the reaction be controlled and correlated within these ranges such that the calculated stability factor F is at least about 850 since this will provide the smallest rate of loss of catalyst activity.

EXAMPLE 1-33

These examples illustrate the effect of the reactant gases, hydrogen and carbon monoxide, temperature and free triarylphosphine:rhodium metal mole ratio on the deactivation of a rhodium hydroformylation catalyst. The procedure employed in Examples 1-19 was as follows. To about 20 grams of an isobutyraldehyde trimer solvent, Filmer 351 (a tradename of Union Carbide) in a high pressure stainless steel reactor, was added a sufficient amount of a rhodium catalyst precursor and triphenylphosphine to provide the free triphenylphosphine:rhodium metal mole ratios shown in Table I below. The reactor was attached to a gas manifold and heated to the temperature shown in Table I. Carbon monoxide and hydrogen were then added to the partial pressures shown in Table I, and the temperature was maintained for the time indicated in Table I, after which the solution was allowed to cool. The resulting solution was then exposed to an equimolar mixture of propylene, hydrogen and carbon monoxide at 100° C. and the rate $(r_1)$ of butyraldehyde formation in gram-mole/liter-hour was determined. The rate $(r_2)$ of butyraldehyde formation was also determined for an identical catalyst solution which had not been exposed to the deactivating conditions.

Examples 20-23 were performed in a similar manner except that a larger volume of solution was exposed to the deactivating conditions and aliquots were taken periodically during this time and tested for activity in the same manner.

The results are shown in Table I below:

TABLE I

| | Deactivation Conditions | | | | |
|---|---|---|---|---|---|
| Ex. | Time (hr) | Temp. (°C.) | CO Partial Pressure (psia) | H₂ Partial Pressure (psia) | TPP/Rh[1] | Observed[2] Activity (%) |
| 1 | 48 | 130 | 40 | 160 | 25 | 2 |
| 2 | 4 | 130 | 40 | 160 | 36 | 14 |
| 3 | 24 | 110 | 40 | 160 | 8 | 11 |
| 4 | 20 | 100 | 40 | 160 | 78 | 55 |
| 5 | 24 | 100 | 20 | 160 | 78 | 61 |
| 6 | 10 | 90 | 10 | 80 | 25 | 87 |
| 7 | 10 | 120 | 10 | 80 | 25 | 33 |
| 8 | 30 | 90 | 10 | 160 | 100 | 79 |
| 9 | 30 | 120 | 35 | 70 | 100 | 19 |
| 10 | 30 | 90 | 55 | 80 | 25 | 42 |
| 11 | 20 | 100 | N₂ | | 78 | 98 |
| 12 | 4 | 130 | N₂ | | 78 | 90 |
| 13 | 4 | 130 | 0 | 40 | 78 | 47 |
| 14 | 4 | 130 | 0 | 40 | 78 | 51 |
| 15 | 24 | 130 | 0 | 160 | 78 | 24 |
| 16 | 24 | 100 | 55 | 0 | 78 | 58 |
| 17 | 20 | 100 | 55 | 0 | 78 | 73 |
| 18 | 22 | 100 | 40 | 0[3] | 78 | Greater than 100 |
| 19 | 20 | 100 | 50 | 0[4] | 78 | Greater than 100 |
| 20 | 4 | 115 | 42.5 | 42.5 | 79 | 47 |
| 21 | 24 | 115 | 42.5 | 42.5 | 79 | 15 |
| 22 | 4 | 115 | 42.5 | 42.5 | 131 | 86 |
| 23 | 24 | 115 | 42.5 | 42.5 | 131 | 22 |
| 24 | 4 | 115 | 42.5 | 42.5 | 157 | 71 |
| 25 | 24 | 115 | 42.5 | 42.5 | 157 | 42 |
| 26 | 4 | 115 | 50 | 25 | 79 | 59 |
| 27 | 6 | 115 | 50 | 25 | 79 | 47 |
| 28 | 4 | 115 | 25 | 50 | 79 | 70 |
| 29 | 6 | 115 | 25 | 50 | 79 | 50 |
| 30 | 4 | 115 | 50 | 0 | 79 | 35 |
| 31 | 6 | 115 | 50 | 0 | 79 | 50 |
| 32 | 2 | 115 | 0 | 50 | 79 | 80 |
| 33 | 6 | 115 | 0 | 50 | 79 | 75 |

[1]TPP/Rh = free triphenylphosphine:rhodium metal mole ratio
[2]Observed activity = $(r_1/r_2) \times 100$
[3] and [4] = propylene present in an amount sufficient to give a partial pressure of 55 and 15 psia, respectively While none of Examples 1-33 illustrates a process of hydroformylation according to the present invention, since one or more of the reactant gases (olefin, hydrogen or carbon monoxide) are not present, the data in Table I indicate that lower partial pressures of carbon monoxide (compare Examples 26 and 28), lower temperatures (compare Examples 6 and 7) and higher free triarylphosphine:rhodium metal mole ratios (compare Examples 20 and 22) favor catalyst stability (the more stable catalysts being indicated in the table by the higher observed activity values). Examples 18 and 19 illustrate the effect of the presence of olefin on the stability of the catalyst.

EXAMPLES 34-48

The following Table II indicates the rate of loss of activity for a rhodium hydroformylation catalyst under hydroformylation conditions. The stability factor shown in the table was calculated using the formula set forth hereinabove and the indicated conditions of the respective Examples. The activity loss was determined by measuring the rate of production of aldehyde in gram-moles/liter-hour at a given time and comparing the measured value against the rate of aldehyde production for the fresh catalyst. The reaction conditions are given in Table II.

TABLE II

| Example | Temperature (°C.) | CO partial pressure (psia) | H₂ partial pressure (psia) | alpha-olefin | alpha-olefin partial pressure (psia) | TPP/Rh[1] | Stability Factor | Lost Activity (% per day) |
|---|---|---|---|---|---|---|---|---|
| 34 | 110 | 91.2 | 62.2 | ethylene | 6.6 | 1300 | 990 | .2 |
| 35 | 100 | 22 | 75 | propylene | 35 | 94 | 660 | 1.6 |
| 36 | 100 | 36 | 75 | " | 40 | 94 | 570 | 3.0 |
| 37 | 100 | 23 | 90 | " | 36 | 105 | 680 | 2.0 |
| 38 | 105 | 19 | 90 | " | 49 | 105 | 620 | 2.7 |
| 39 | 90 | 10.6 | 85 | " | 35 | 100 | 860 | .2 |
| 40 | 100 | 10.6 | 85 | " | 35 | 100 | 740 | 1.0 |
| 41 | 110 | 8 | 106 | " | 33 | 97 | 570 | 2.3 |
| 42 | 105 | 7.5 | 110 | " | 45 | 200 | 860 | 0.2 |
| 43 | 110 | 7.5 | 110 | " | 35 | 200 | 820 | 0.3 |
| 44 | 115 | 10 | 110 | " | 35 | 200 | 660 | 1.0 |
| 45 | 120 | 7.5 | 110 | " | 39 | 200 | 670 | 2.0 |
| 46 | 105 | 7.5 | 125 | " | 40 | 200 | 870 | .1 |
| 47[2] | 120 | 11 | 75 | " | 35 | 200 | 640 | 28. |

TABLE II-continued

| Example | Temperature (°C.) | CO partial pressure (psia) | H₂ partial pressure (psia) | alpha-olefin | alpha-olefin partial pressure (psia) | TPP/Rh[1] | Stability Factor | Lost Activity (% per day) |
|---|---|---|---|---|---|---|---|---|
| 48[3] | 120 | 11 | 75 | " | 35 | 200 | 640 | 99 |

[1]TPP/Rh = same as in Table I
[2]synthesis gas (H₂ + CO) contained 6 ppm H₂S and 5 ppm COS
[3]synthesis gas contained 24 ppm H₂S and 52.8 ppm COS Examples 35–46 are within the scope of the present invention and illustrate the relationship between the reaction conditions, the stability factor F and the stability of the catalyst. Example 34 illustrates the fact that the olefin ethylene has more of a catalyst stabilizing effect than propylene. In Example 34, the carbon monoxide partial pressure is higher than in the present invention but a stable catalyst is obtained due to the very high phosphine/rhodium ratio employed, and also due to the fact that ethylene enhances the stability of the catalysts more than other olefins. Examples 47 and 48 are not considered to be within the invention in view of the presence in the synthesis gas of the sulfur impurities.

EXAMPLES 49–52

These Examples indicate the deactivation of rhodium hydroformylation catalysts expressed in terms of the change in the rate of the hydroformylation with respect to time. The value of Integrated Turnover Number (ITON) given in Table III is defined as the number of moles of aldehydes formed per mole of rhodium metal in the catalyst and is an abstract measure of catalyst life. The reaction conditions and results are shown in Table III below. Examples 49, 50 and 52 illustrate the process of the present invention insofar as they illustrate the effect of different olefins on catalyst stability. Example 51 employs an internal olefin which is not intended to be within the scope of the present invention.

TABLE III

| Example | Temperature (°C.) | CO partial pressure (psia) | H₂ partial pressure (psia) | olefin | olefin partial pressure (psia) | TPP/Rh[1] | ITON[2] | Activity %[3] |
|---|---|---|---|---|---|---|---|---|
| 49 | 80 | 29 | 26 | propylene | 17 | 15 | 3.5 × 10² | 37 |
| 50 | 80 | 29 | 26 | ethylene | 17 | 15 | 3.4 × 10³ | 77.5 |
| 51 | 120 | 62 | 77 | 2-butene | 68 | 6 | 7.2 × 10² | 5 |
| 52 | 110 | 20 | 71 | 1-butene | 40 | 12 | 1.1 × 10³ | 58 |

[1]TPP/Rh = same as in Table I
[2]ITON = Integrated turnover number
[3]% Activity = rate at end of reaction compared to rate at beginning of the reaction

What is claimed is:

1. In a process for hydroformylating an alpha-olefin having from 2 to 20 carbon atoms to produce aldehydes having one more carbon atom than the alpha-olefin by reacting the alpha-olefin with hydrogen and carbon monoxide in the presence of a rhodium complex catalyst consisting essentially of rhodium complexed with carbon monoxide and a triphenylphosphine, and in the presence of free triphenylphosphine the improvement comprising operating said process at a temperature of from about 90° to about 130° C., a partial pressure of carbon monoxide of less than about 55 pounds per square inch absolute, a partial pressure of hydrogen of less than about 200 pounds per square inch absolute, a total gas pressure of hydrogen, carbon monoxide and alpha-olefin of less than about 400 pounds per square inch absolute, and at least about 100 moles of free triphenylphosphine per mole of catalytically-active rhodium metal; and minimizing or substantially preventing deactivation of said rhodium complex catalyst to a maximum determined rate of loss of activity by controlling and correlating the carbon monoxide partial pressure, the temperature and the free triphenylphosphine:catalytically-active rhodium metal mole ratio within said values to provide the minimum stability factor F necessary to give essentially the minimum rate of loss of activity according to FIG. 1 of the drawings;

said stability factor F being defined by the equation:

$$F = \frac{1000}{1 + e^Y}$$

where
F = stability factor,
e = Naperian log base (2.718281828),
y = $K_1 + K_2T + K_3P + K_4(L/Rh)$,
$K_1 = -8.1126$,
$K_2 = 0.07919$,
T = the reaction temperature (°C.),
$K_3 = 0.0278$,
P = the carbon monoxide partial pressure (psia),
$K_4 = -0.01155$, and
(L/Rh) = the free triphenylphosphine:catalytically-active rhodium metal mole ratio.

2. The process of claim 1, wherein said alpha-olefin has from 2 to 5 carbon atoms.

3. The process of claim 1, wherein said alpha-olefin is propylene.

4. The process of claim 1, wherein said alpha-olefin is ethylene.

5. The process of claim 1, wherein said alpha-olefin is 1-butene.

6. The process of claim 1, wherein the partial pressure of carbon monoxide is from about 2 to about 20 pounds per square inch absolute.

7. The process of claim 1, wherein the temperature is from about 90° to about 120° C.

8. The process of claim 1, wherein the free triphenylphosphine:catalytically-active rhodium metal mole ratio is at least about 50.

9. The process of claim 1, wherein the total gas pressure of hydrogen, carbon monoxide and alpha-olefin is less than about 350 pounds per square inch absolute.

10. The process of claim 1, wherein the partial pressure of hydrogen is from about 60 to about 160 pounds per square inch absolute.

11. The process of claim 1, wherein the ratio of the partial pressures of hydrogen:carbon monoxide is at least about 2:1.

12. The process of claim 1, wherein the ratio of the partial pressures of hydrogen:carbon monoxide is at least about 8:1.

13. The process of claim 1, wherein said catalyst is dissolved in a solvent which comprises the high boiling liquid condensation products of said aldehydes.

14. The process of claim 1, wherein the maximum determined rate of loss of activity of said catalyst is 0.75 percent per day.

15. The process of claim 1, wherein said minimum stability factor F is about 850.

16. The process as defined in claim 1, wherein the partial pressure of carbon monoxide is from about 2 to about 20 pound per square inch absolute, wherein the partial pressure of hydrogen is from about 60 to about 160 pounds per square inch absolute, wherein the total gas pressure of hydrogen, carbon monoxide and alpha-olefin is less than about 350 pounds per square inch absolute, and wherein the free triphenylphosphine:catalytically-active rhodium metal ratio ranges from about 150 to about 300 moles of free triphenylphosphine per mole of catalytically-active rhodium metal.

17. The process as defined in claim 16, wherein the alpha-olefin is propylene and wherein the stability factor F is about 850.

* * * * *

UNITED STATES PATENT AND TRADEMARK OFFICE
CERTIFICATE OF CORRECTION

PATENT NO. : 4,277,627
DATED : July 7, 1981
INVENTOR(S) : D.R. Bryant and E. Billig It is certified that error appears in the above-identified patent and that said Letters Patent are hereby corrected as shown below:

The aldol formula in column 3, lines 64 to 67 should be identified as --Aldol (IX)--.

Column 5, line 45 --poisons-- is misspelled.

Claim 8, line 3 (column 21) the value "50" should be ---150---.

Signed and Sealed this

Eighth Day of December 1981

[SEAL]

Attest:

*Attesting Officer*

GERALD J. MOSSINGHOFF

*Commissioner of Patents and Trademarks*